United States Patent
Stieber et al.

(10) Patent No.: US 6,906,121 B2
(45) Date of Patent: Jun. 14, 2005

(54) 4-NITROSODIPHENYLAMINE DERIVATIVES AND THEIR USE AS COUPLING AGENTS FOR FILLED RUBBER COMPOUNDS

(75) Inventors: Joseph F. Stieber, Prospect, CT (US); Franklin H. Barrows, Waterbury, CT (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 254 days.

(21) Appl. No.: 10/395,591

(22) Filed: Mar. 24, 2003

(65) Prior Publication Data

US 2004/0192826 A1 Sep. 30, 2004

(51) Int. Cl.$^7$ .............................. C08K 5/34; C08K 5/32
(52) U.S. Cl. .............................. 524/83; 524/91; 524/94; 524/99; 524/100; 524/238; 524/240; 524/259; 524/260; 524/424; 252/401; 252/402; 252/403
(58) Field of Search .............................. 524/83, 91, 94, 524/99, 100, 238, 240, 259, 260, 424; 252/401, 402, 403

(56) References Cited

U.S. PATENT DOCUMENTS

| | | | |
|---|---|---|---|
| 4,557,306 A | 12/1985 | Graves | 152/548 |
| 4,570,690 A | 2/1986 | Graves | 152/564 |
| 4,751,271 A | 6/1988 | Graves | 525/329.3 |
| 4,788,229 A | 11/1988 | Bohm et al. | 523/215 |
| 6,642,315 B2 * | 11/2003 | Amino et al. | 525/232 |

OTHER PUBLICATIONS

Morita, E. Rubber Chem. Technol, 49(4), 1019–1030, (1976).
Stefanowski, T. Polimery, 12(12), 571–573 (1967).
Devrits, Y. et al., Kauch. Rezina, 26(3), 14–17 (1967).
Walker, LA & Kerwood, JE, Rubber Age, 90(6), 925–931 (1962).
Leeper, HM, Gable, CL, D'Amico, JJ & Tung, CC, Rubber World, 413–428, Dec. (1956).
Graves, D.F., Rubber Chem. and Technol, 66(1), 61–72 (1993).
Ceausescu, E. et al., J. Macromol. Sci., A22 (5–7), 1013–1032 (1985).
Zyuzin, A.P., Kauch. Rezina, 1983 (10), 11–13.
Shvarts, V. et al., Kauch. Rezina, 1982(6), 24–26.

* cited by examiner

*Primary Examiner*—Kriellion A. Sanders
(74) *Attorney, Agent, or Firm*—Michael P. Dilworth

(57) ABSTRACT

A composition of matter is disclosed that comprises a compound of the formula $A_nR$, wherein:

A is

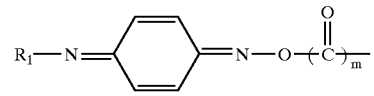

$R_1$ is hydrocarbyl;
m is 0 or 1;
n is 1, 2, or 3;
R is selected from the group consisting of:
mono-, di-, and trivalent aliphatic groups; mono-, di-, and trivalent aromatic groups; five- and six-membered heterocyclic rings comprising n carbon atoms bonded to A, at least one nitrogen atom, and, optionally, at least one sulfur atom; and

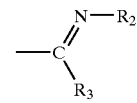

wherein $R_2$ and $R_3$ are independently selected from the group consisting of hydrogen and hydrocarbyl. These compounds are useful as coupling agents in filled elastomer compositions.

43 Claims, No Drawings

4-NITROSODIPHENYLAMINE DERIVATIVES AND THEIR USE AS COUPLING AGENTS FOR FILLED RUBBER COMPOUNDS

BACKGROUND OF THE INVENTION

1. Field of the Invention

The present invention relates to 4-nitrosodiphenylamine derivatives that are useful as coupling agents for carbon black filled rubber compounds.

2. Description of Related Art

Fillers, such as carbon black, are added to elastomeric compounds for a variety of reasons. They act as low cost diluents and as reinforcing agents, giving higher modulus, higher strength and wear resistance. The interaction between a filler and an elastomer matrix is also very important to the development of desirable dynamic properties. It is known that dynamic properties are improved when a carbon black filler is bonded to an elastomer matrix. This is evidenced by lower hysteresis, which results in lower rolling resistance when the rubber is used to make automobile tires. An additional benefit of better elastomer-filler interaction is improved traction when the rubber is used in tire treads. Improved bonding between the polymer and filler can also result in a cured rubber exhibiting lower heat build-up.

In the absence of interaction between the filler and the elastomeric matrix, the filler forms a loosely bonded network within the matrix, which remains after curing. When the dynamic storage modulus, designated G', is measured in the cured rubber sample, the filler network acts to increase the modulus. As the applied strain on the rubber sample is increased, the bonds that form this filler network are broken and it no longer contributes to the modulus. Thus, in the absence of coupling between the filler and the elastomer matrix, the dynamic storage modulus, G', will diminish as an applied strain is increased. This is known as the Payne Effect.

When the filler and the elastomer matrix are coupled, no filler network forms in the cured elastomer. Thus, when an applied strain is increased as the dynamic measurement is made, the storage modulus, G', does not decrease as rapidly with an increase in the strain. This diminution of the Payne Effect is also taken as evidence that coupling has taken place.

In the past, some chemicals have been added to rubber to improve the interaction of carbon black with the rubber matrix. For example, N-methyl-N,4-dinitrosoaniline was used, but it was discontinued due to concerns about its toxicity. Benzofurazan oxides have also been reported to be effective coupling agents, but upon curing they evolve an undesirable odor.

The use of 4-nitrosodiphenylamine as a promoter for the interaction of carbon black and rubber has also been suggested. The chemical is an effective promoter, but its usefulness is limited by a pronounced tendency to affect the processability of the rubber by dramatically reducing the scorch safety of the rubber compound.

U.S. Pat. No. 4,557,306 discloses carbon black products, said to be useful in rubber compositions, and rubber compositions (uncured or cured) containing said carbon black products comprising carbon black having a surface area of at least 20 m²/g. and up to about 10% by weight, based on the weight of the carbon black of at least one aromatic furazan oxide. Useful furazan oxides have both carbons of the furazan ring as part of a fused aromatic ring, and particular examples include benzofurazan oxide, and its methyl and methoxy analogs. It is disclosed that filled rubber vulcanizates containing the carbon black products exhibit many improved properties, such as increased filler-rubber interaction and decreased hysteresis, and that tires made from them show lower running temperatures and improved rolling resistance.

U.S. Pat. No. 4,570,690 discloses filled rubber vulcanizates containing aromatic furazan oxides that are said to exhibit many improved properties, such as increased filler-rubber interaction and decreased hysteresis. Useful furazan oxides have both carbons of the furazan ring as part of a fused aromatic ring. Typical examples are benzofurazan oxide and its methyl and methoxy analogs. It is further disclosed that tires made from the vulcanizates show lower running temperatures and improved rolling resistance and that the desirable effects of the aromatic furazan oxides may be improved by mixing the rubber, filler and furazan oxide in a conventional mechanical compounding device at specific temperatures and time periods, such as about 200°–400° F. for 2–20 minutes.

U.S. Pat. No. 4,751,271 discloses modified polymer rubber compositions prepared in solution that are said to exhibit desirable properties, particularly when used to form tires. The modified rubber compositions comprise the reaction product, prepared in solution, of at least one rubber having an unsaturated carbon chain and up to about 10 weight percent, based on the weight of the rubber, of at least one aromatic furazan oxide of the partial formula

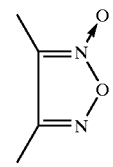

wherein the depicted carbon atoms are a part of a single fused aromatic ring. The reaction is conducted by heating the solution at an elevated temperature which may be any temperature up to the decomposition temperature of the furazan oxide. The uncured polymer rubber compositions do not have the strong characteristic odor of the furazan oxide decomposition products which facilitate handling and storage of these materials. Filled vulcanizates also are described, and these vulcanizates are prepared by vulcanizing a composition comprising at least one of the above-described uncured polymer rubber compositions and one or more reinforcing fillers normally used in rubber compounding. It is further disclosed that the filled vulcanizates exhibit desirable properties such as decreased hysteresis, increased rebound and, when used in the tread of tires, the tires show lower running temperatures and reduced rolling resistance.

U.S. Pat. No. 4,788,229 discloses that uncured modified rubber compositions can be prepared by a process which comprises the steps of (A) preparing a first mixture comprising an elastomer, at least one reinforcing filler and at least one chemical agent capable of promoting the formation of filler-elastomer linkages; (B) preparing a second mixture comprising (i) an elastomer, at least one reinforcing filler and at least one chemical agent capable of promoting the formation of filler-elastomer linkages, wherein at least one of the elastomer, filler or chemical agent in the second mixture is different from the elastomer, filler or chemical agent in the first mixture; or (ii) an elastomer and at least one reinforcing filler; or (iii) at least one reinforcing filler and at least one chemical agent capable of promoting the formation of filler-elastomer linkages; or (iv) an elastomer and at least one chemical agent capable of promoting the formation of filler-elastomer linkages; and (C) blending the first and second mixtures to form a third mixture. Examples of such chemical agents include aromatic furazan oxides, heterocyclic di-N-oxides, 1-hydroxy-benzimidazole-3-oxide compounds, 1,3-dihydroxy-benzimidazolinone compounds, and aromatic nitroso compounds.

Morita, E., *Rubber Chem. Technol*, 49(4):1019–30 (1976) elucidated the mechanism of reactions of N,4-dinitroso-N-methylaniline (DNMA) with polymers and its promotion of carbon black reinforcement in polymers by spectrophotometric observations of the factors that influence these reactions and the functionality of the two dissimilar nitroso groups of DNMA.

Stefanowski, T., *Polimery*, 12(12):571–3 (1967) coated carbon black with couplers, then extracted with benzene to remove uncombined material, then compounded into rubber. N,4-dinitroso-N-methylaniline, dihydroxynitrosobenzoquinone (Vulkafor BQN), pentachlorothiophenol, hexachlorocyclopentadiene, 2,6-dichloro-4-nitrophenol, and tetrachloroquinone were tested. Pentachlorothiophenol and hexachlorocyclopentadiene increased interaction of the carbon black with rubber. See CA 69: 20179t.

Devrits, Y. et al., *Kauch. Rezina*, 26(3):14–17 (1967), disclosed that carbon black in rubber with N,4-dinitroso-N-methylaniline gives improved properties, including heat build up. CA 67: 22668j Walker, L. A. et al., *Rubber Age*, 90(6):925–931 (1962), disclosed that the use of N,4-dinitroso-N-methylaniline in natural rubber, SBR-, and NR-SBR-carbon black stocks brings about increased modulus, reduced hysteresis, and lower heat build-up. The reaction was carried out in a Banbury mixer by simultaneous mixing of the chemical with rubber and carbon black at a temperature of 150° C.

Leeper, H. M. et al., *Rubber World*, December 1956 pp. 413–428, disclosed that the properties of butyl rubber vulcanizates can be improved by chemical modification of the polymer with N-methyl-N,4-dinitrosoaniline.

Graves, D. F., *Rubber Chem. and Technol*, 66(1):61–72 (1993), showed that benzofuran 1-oxide, commonly called benzofuroxan (BFO), decreased hysteresis of carbon black-filled rubber vulcanizates by as much as 30%. BFO was added during the mixing of the masterbatch at various temperatures. It was found that high temperature mixing was necessary to achieve maximum hysteresis reduction and that more effect was noted with high surface are blacks. Nickel salts were found to modify the reaction between BFO and the elastomer/black.

Ceausescu, E. et al., *J. Macromol. Sci.-Chem*, A22(5–7):1013–32 (1985), explained the mechanism of the action of nitroso derivatives on the basis of the theory that the reinforcing effect is due to the strain-crystallization process. CA 103: 23606m Zyuzin, A. P., *Kauch. Rezina*, 1983 (10):11–13, showed that the addition of p-nitrosodiphenylamine enhanced the absorption of SKI-3 rubber on the surface of carbon black and reduced hysteresis losses. The modification of PM-100 black-filled isoprene tread rubbers with oligodienes decreased the content of bound rubber and increased hysteresis losses, presumably due to competing adsorption of rubber and oligodiene macromolecules on the surface of the carbon black. CA 99: 213920f Shvarts, V. et al., *Kauch. Rezina*, 1982(6):24–6, disclosed that SKI or SKD rubber modified with p-nitrosodiphenylamine gives better properties including resilience, tear, tensile, modulus. A three-pass mix with separate introduction of carbon black is required. CA 97: 56916y.

SUMMARY OF THE INVENTION

The most practical and useful promoters of the interaction between carbon black and rubber will be those that have a minimal impact on the other properties of the rubber compound. That is, they will not have a dramatic effect on the scorch safety or the cure rate of the rubber, either by substantially increasing or decreasing the cure rate or scorch time. Also, they should have a minimal effect on the viscosity of the uncured rubber compound. Neither will they substantially increase the modulus of the cured rubber. Similarly, the elongation at break should not be dramatically reduced.

Compounds of the formula $A_nR$ have been found to be useful as coupling agents for carbon black filters in unsaturated rubber, wherein:

A is

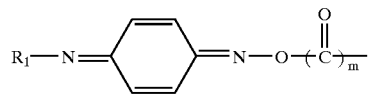

$R_1$ is hydrocarbyl;

m is 0 or 1;

n is 1, 2, or 3;

R is selected from the group consisting of:
mono-, di-, and trivalent aliphatic groups; mono-, di-, and trivalent aromatic groups; five- and six-membered heterocyclic rings comprising n carbon atoms bonded to A, at least one nitrogen atom, and, optionally, at least one sulfur atom; and

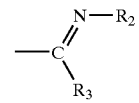

wherein $R_2$ and $R_3$ are independently selected from the group consisting of hydrogen and hydrocarbyl.

More particularly, the present invention is directed to a composition of matter comprising a compound of the formula $A_nR$,
wherein:

A is

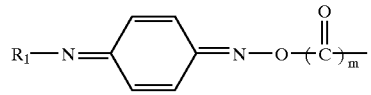

$R_1$ is hydrocarbyl;

m is 0 or 1;

n is 1, 2, or 3;

R is selected from the group consisting of:
mono-, di-, and trivalent aliphatic groups; mono-, di-, and trivalent aromatic groups; five- and six-membered heterocyclic rings comprising n carbon atoms bonded to A, at least one nitrogen atom, and, optionally, at least one sulfur atom; and

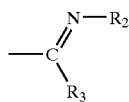

wherein $R_2$ and $R_3$ are independently selected from the group consisting of hydrogen and hydrocarbyl.

In another aspect, the present invention is directed to a composition of matter comprising an elastomer, a filler, and a compound of the formula $A_nR$, wherein:

A is

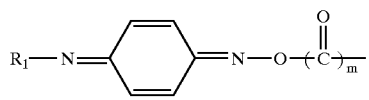

$R_1$ is hydrocarbyl;
m is 0 or 1;
n is 1, 2, or 3;
R is selected from the group consisting of mono-, di-, and trivalent aliphatic groups; mono-, di-, and trivalent aromatic groups; five- and six-membered heterocyclic rings comprising n carbon atoms bonded to A, at least one nitrogen atom, and, optionally, at least one sulfur atom; and

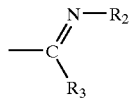

wherein $R_2$ and $R_3$ are independently selected from the group consisting of hydrogen and hydrocarbyl.

In still another aspect, the present invention is directed to an article of manufacture comprising a cured mixture comprising an elastomer, a filler, and a compound of the formula $A_nR$, wherein:

A is

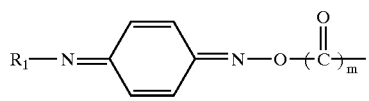

$R_1$ is hydrocarbyl;
m is 0 or 1;
n is 1, 2, or 3;
R is selected from the group consisting of:
mono-, di-, and trivalent aliphatic groups; mono-, di-, and trivalent aromatic groups; five- and six-membered heterocyclic rings comprising n carbon atoms bonded to A, at least one nitrogen atom, and, optionally, at least one sulfur atom; and

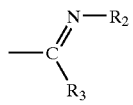

wherein $R_2$ and $R_3$ are independently selected from the group consisting of hydrogen and hydrocarbyl. Preferably, the article is a tire tread.

DESCRIPTION OF THE PREFERRED EMBODIMENTS

As noted above, the compositions of the present invention comprise a compound of the formula $A_nR$, wherein:

A is

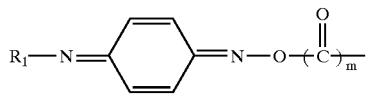

$R_1$ is hydrocarbyl;
m is 0 or 1;
n is 1, 2, or 3;
R is selected from the group consisting of:
mono-, di-, and trivalent aliphatic groups; mono-, di-, and trivalent aromatic groups; five- and six-membered heterocyclic rings comprising n carbon atoms bonded to A, at least one nitrogen atom, and, optionally, at least one sulfur atom; and

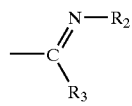

wherein $R_2$ and $R_3$ are independently selected from the group consisting of hydrogen and hydrocarbyl.

As employed herein, the term "hydrocarbyl" includes hydrocarbon as well as substantially hydrocarbon groups. "Substantially hydrocarbon" describes groups which contain heteroatom substituents that do not alter the predominantly hydrocarbon nature of the group. Examples of hydrocarbyl groups include the following:

(1) hydrocarbon substituents, i.e., aliphatic (e.g., alkyl or alkenyl), alicyclic (e.g., cycloalkyl, cycloalkenyl) substituents, aromatic substituents, aromatic-, aliphatic- and alicyclic-substituted aromatic substituents, and the like, as well as cyclic substituents wherein the ring is completed through another portion of the molecule (that is, for example, any two indicated substituents may together form an alicyclic radical);

(2) substituted hydrocarbon substituents, i.e., those substituents containing non-hydrocrabon groups which, in the context of this invention, do not alter the predominantly hydrocarbon nature of the substituent; those skilled in the art will be aware of such groups (e.g., halo, hydroxy, mercapto, nitro, nitroso, sulfoxy, etc.);

(3) heteroatom substituents, i.e., substituents which will, while having a predominantly hydrocarbon character within the context of this invention, contain an atom other than carbon present in a ring or chain otherwise composed of carbon atoms (e.g., alkoxy or alkylthio). Suitable heteroatoms will be apparent to those of ordinary skill in the art and include, for example, sulfur, oxygen, nitrogen, and such substituents as, e.g., pyridyl, furyl, thienyl, imidazolyl, etc. Preferably, no more than about 2, more preferably no more than one, hetero substituent will be present for every ten carbon atoms in the hydrocarbyl group. Most preferably, there will be no such heteroatom substituents in the hydrocarbyl group, i.e., the hydrocarbyl group is purely hydrocarbon.

In the formula $A_nR$ described above, $R_1$ is hydrocarbyl. Examples of $R_1$ include, but are not limited to, unsubstituted phenyl;

phenyl substituted with one or more alkyl groups, such as methyl, ethyl, propyl, butyl, pentyl, hexyl, heptyl, octyl, nonyl, decyl, isomers of the foregoing, and the like;

phenyl substituted with one or more alkoxy groups, such as methoxy, ethoxy, propoxy, butoxy, pentoxy, hexoxy, heptoxy, octoxy, nonoxy, decoxy, isomers of the foregoing, and the like;

phenyl substituted with one or more alkyl amino or aryl amino groups;

naphthyl and alkyl substituted naphthyl;

straight chain or branched chain alkyl groups containing from one to twelve carbons atoms, such as methyl, ethyl, propyl, butyl, pentyl, hexyl, heptyl, octyl, nonyl, decyl, undecyl, and dodecyl, and isomers of the foregoing; and cyclic alkyl groups, such as cyclopentyl, cyclohexyl, cycloheptyl, cyclooctyl, and cyclododecyl.

$R_2$ and $R_3$ can be the same or different and can be hydrogen or hydrocarbyl, as described above for $R_1$.

Where R is a five- or six-membered heterocyclic ring containing one or more carbon atoms, one or more nitrogen atoms, and, optionally, one or more sulfur atoms, such ring may be fused to a benzene ring. Such five- or six-membered heterocyclic rings include, but are not limited to, imidazole, pyrrole, isopyrrole, 3-isopyrrole, pyrazole, 2-isoimidazole, 1,2,3-triazole, 1,2,4-triazole, thiazole, isothiazole, pyridine, pyridazine, pyrimidine, pyrazine, 1,3,5-triazine, 1,2,4-triazine, 1,2,3-triazine, indole, indolenine, 2-isobenzazole, isoindazole, quinoline, isoquinoline, cinnoline, quinazoline, and the like.

Where R is such a five- or six-membered ring, it is preferred that it be selected from the group consisting of 1,3,5-triazinyl, 2-imidazolyl, 2-pyridinyl, 2-pyrimidinyl, 2-pyrazinyl, 3-pyridazinyl, 2-thiazolyl, 2-quinolyl, 2-quinoxalinyl, 2-quinazolinyl,2-benzimidazolyl, and 2-benzothiazolyl.

When the heterocyclic ring is a 1,3,5-triazine ring, and n is 1 or 2, the triazine ring may also be substituted with groups, such as hydroxy, alkoxy, halo, amino, alkyl amino, or phenyl amino.

R in the above formula may also be an aliphatic or aromatic group. In the case where R is an aliphatic group, it may be mono-, di-, or trivalent.

Examples of monovalent aliphatic groups include alkyl groups, such as methyl, ethyl, propyl, butyl, pentyl, hexyl, heptyl, octyl, nonyl, decyl, undecyl, dodecyl, tetradecyl, hexadecyl, octadecyl, isomers of the foregoing, and the like; substituted alkyl groups, such as benzyl and 1- or 2-phenylethyl; alkenyl and alkylidene groups, such as ethylidene, (an acrylic acid derivative), 1-methylethylidene, (a methacrylic acid derivative), 1-heptadec-8-enyl, (an oleic acid derivative), and 1-heptadeca-8,11-dienyl, (a linoleic acid derivative).

Examples of divalent groups include nothing, i.e., the case where the compound is an oxalic acid derivative and n is 1 or 2, methylene, 1,2-ethylene, 1,2-ethylidene, 1,3-propylene, 1,4-butylene, 1,5-pentylene, and the like.

Examples of trivalent groups include, but are not limited to, propane-1,2,3-triyl, 2-hydroxypropane-1,2,3-triyl, and propene-1,2,3-triyl.

In the case where R is an aromatic group, it may also be mono-, di-, or trivalent.

Examples of monovalent aromatic groups include, but are not limited to, phenyl, 2-, 3-, or 4-tolyl, xylyl (various isomers), 2- or 4-decylphenyl, 2- or 4-dodecylphenyl, 2- or 4-alkoxycarbonylphenyl, 2- or 4-carboxyphenyl, 2- or 4-hydroxyphenyl, 2- or 4-alkoxyphenyl, 2- or 4-aminophenyl, 2- or 4-alkylaminophenyl, and the like.

Examples of divalent aryl groups include, but are not limited to, 1,2-disubstituted phenyl, 1,3-disubstituted phenyl, 1,4-disubstituted phenyl, and the like.

Examples of trivalent aryl groups include, but are not limited to, 1,3,5-trisubstituted phenyl, 1,2,4-trisubstituted phenyl, and the like.

When added to carbon black filled rubber compounds during a first mixing step, the compositions of the present invention produce vulcanizates that have superior dynamic properties. That is, they have lower hysteresis, as measured by tan δ at 60° C. 10 Hz, than rubber compounds mixed in the same manner that do not contain the new compositions. The improved dynamic properties are achieved without also producing a dramatically undesirable effect on the other properties of the rubber compound, such as cure rate, modulus, and tensile strength.

The above-described benefits may be realized by mixing the compounds of the present invention, with an unsaturated elastomeric polymer, along with carbon black filler, at a temperature and for a time sufficient to effect an interaction between the polymer and the filler. Typically, this will be done in the first step of a multi-step mixing process intended to produce an uncured rubber compound ready for vulcanization. The time and temperature required to produce the interaction may be varied, depending on the particular compound used, the polymer or blend of polymers used, and the particular set of properties desired. Generally, the temperature will be above 300° F. (about 149° C.), and usually above 320° F. (160° C.). Better results may be obtained by mixing at temperatures of 340° F. ( about 171° C.) or higher. The mixing time may also be varied according to circumstances. Generally, the best results will be obtained with a mix time of about one to three minutes or more. Mixing rubber, filler, and the compounds of the present invention is normally done in a high shear internal mixer, usually a Banbury or similar mixer.

The rubber may be a single polymer, or a blend of different polymers. Polymers that can be used include, but are not limited to, emulsion polymerized styrene-butadiene rubber, solution polymerized styrene-butadiene rubber, polybutadiene, natural rubber, polyisobutylene, and polyisoprene.

The compounds of the present invention may be added to the rubber compound at a level of from about 0.1 to about 10 phr, (parts per hundred of rubber polymer). Preferably, they are added at a level of from about 1.0 to about 5.0 phr.

The carbon blacks suited useful in the practice of the present invention are those normally used in elastomeric compounds. These are carbon blacks with Nitrogen Surface Areas of $10-250 \times 10^3$ m$^2$/kg, as determined by ASTM D4820. The structure or DBP Number of the black should measure from $10-250 \times 10^{-5}$ m$^3$/kg by ASTM D2414.

Other compounding ingredients may be included in the rubber compound according to the intended use of the vulcanizate. These include antidegradants, such as p-phenylenediamine antiozonants, diphenylamine based antioxidants, extending oils, and waxes. The rubber compounds may be cured using normal sulfur vulcanizing ingredients, such as sulfur or a sulfur donor, zinc oxide, stearic acid, or zinc stearate, and vulcanization accelerators. These ingredients are typically added in subsequent mixing steps, with the curing ingredients being added in the last step.

The compounds of the present invention may be made by the reaction of an appropriate acidic halide or anhydride with an appropriately substituted 4-nitrosoaniline, in the presence of a base.

The advantages and the important features of the present invention will be more apparent from the following examples.

EXAMPLE 1

Preparation of 2,4,6-tris(N-phenyl-p-benzoquinonediiminoxy)-1,3,5-triazine

A solution was prepared by dissolving 29.7 grams, (0.15 mole), of 4-nitrosodiphenylamine in 100 grams of 6% sodium hydroxide. This solution was placed in a one liter reaction flask equipped with a thermometer, stirrer, reflux condenser, and an addition funnel. Acetonitrile, 400 mL, was added to the flask. A solution was made by dissolving 9.2 grams, (0.05 mole), of cyanuric chloride in 200 mL of acetonitrile. This solution was placed in the addition funnel. The solution in the flask was cooled to 5–10° C. and the solution of cyanuric chloride was added dropwise over a period of one hour. The mixture was allowed to come to room temperature and held for an additional hour. The red precipitate that had formed was filtered, washed with fresh acetonitrile, and dried. The yield was 28 grams, 83.7% of theory, mp 135–138° C.

EXAMPLE 2

Preparation of N-{4[(benzoyloxy)imino]-2,5-cyclohexadien-1-ylidene}aniline

A solution was prepared by dissolving 4-nitrosodiphenylamine, 25.0 grams, (0.126 mole) and triethylamine, 13.4 grams, (0.132 mole) in 300 mL of toluene. The solution was put in a suitable reaction flask and cooled to 5° C. A solution of benzoyl chloride, 17.7 grams, (0.126 mole), was dissolved in 50 mL of toluene and added slowly to the stirred solution of 4-nitrossodiphenylamine. The materials were allowed to react and the triethylamine hydrochloride precipitate was filtered. The toluene solution was concentrated and the product that crystallized was filtered and dried. The yield was 15.96 grams of product melting at 122–124° C.

EXAMPLE 3

Preparation of N-{4[(acetyloxy)imino]-2,5-cyclohexadien-1-ylidene}aniline

A solution was prepared by mixing 4-nitrosodiphenylamine, 19.8 grams, (0.10 mole), pyridine, 8.6 grams, (0.11 mole), and toluene, 10 mL, in a suitable reaction flask. The solution was cooled to 5° C. and acetic anhydride, 11.22 grams, (0.11 mole) was added slowly. The mixture was stirred for 2 hours and allowed to come to room temperature. The reaction mixture was mixed with a quantity of water, allowed to stand until the water layer separated, and the water layer was discarded. The toluene solution was evaporated to leave 21.4 grams of a solid residue, 96% of theory. The material melted at 63–65° C.

Formulations and Materials

The raw materials used in the following examples are all obtained from commercial sources.

SSBR was Solflex 1216, a solution polymerized styrene-butadiene rubber produced by Goodyear Polymers. The styrene content is 12%, the vinyl content is 46% and the $T_g$ is −45° C.

BR was Budene 1207, a polybutadiene rubber produced by Goodyear.

The oil was Sundex 8125, an aromatic processing oil produced by Sun Oil.

Zinc Oxide, produced by the Zinc Corporation of America.

Stearic acid, produced by Monson Chemical.

The 6-PPD was Flexzone 7P (N-(1,3-dimethylbutyl)-N'-phenyl-p-phenylenediamine), commercially available from Uniroyal Chemical Company.

The wax was Sunproof Improved, a microcrystalline wax commercially available from Uniroyal Chemical Company.

The TBBS was Delac NS (N-tert-butyl-2-benzothiazolylsulfenamide) commercially available from Uniroyal Chemical Company.

DPG, diphenylguanidine produced by Akrochem.

Sulfur 21–10, produced by Georgia Gulf

The general mixing procedure is given below:

First Pass:

The rubber, carbon black, promoter, and processing oil are charged to a laboratory internal mixer and mixed for 1.5 minutes. The ram is raised and a sweep performed. The ram is lowered and mixing is continued until a designated temperature is reached. The materials are then mixed for a predetermined time at a designated temperature and then discharged.

Second Pass:

The masterbatch mixed in the first pass is charged to the mixer. Stearic acid, zinc oxide, antiozonant, and wax are added. These ingredients are added in a second pass to avoid possible interference with the promoting process. The materials are mixed for one minute, then the ram is raised and a sweep performed. The ram is lowered and mixing continued until the batch reaches an internal temperature of 138° C., or for a maximum of 5 minutes.

Third Pass:

The masterbatch produced in the second pass is charged to the mixer. The curatives, sulfur and accelerators, are added. The materials are mixed for one minute, then the ram is raised and a sweep performed. The ram is lowered and mixing continued until the batch reaches an internal temperature of 104° C.

Materials for Examples 4–8, were mixed in a Farrel BR1600 internal mixer, with a volume of 1.6 liters. The curing properties were determined on a Model ODR 2000 oscillating disc rheometer. The dynamic properties were determined at 60° C. and 10 Hz over a strain range of 0.2 to 14% using Model RPA 2000 Rubber Process Analyzer.

Standard ASTM test methods were used for measurement of Mooney viscosity (D3346-90), ODR cure characteristics (D2084-92), stress-strain (D412-92), and Shore A hardness (D2240-91).

EXAMPLE 4

In this example, composition A was mixed until the batch reached 340° F. (about 171° C.). Compositions B and C were mixed for three minutes at 340° F. (See, First Pass Mix in Table 1). The second and third pass mixes were carried out according to the procedure outlined above. Test pieces for the stress-strain measurements were cured in a heated press at 160° C. for the times indicated in Table 2.

TABLE 1

|  | A | B | C |
|---|---|---|---|
| First Pass Mix | | | |
| SSBR | 75.0 | 75.0 | 75.0 |
| BR | 25.0 | 25.0 | 25.0 |
| N234 Carbon Black | 72.0 | 72.0 | 72.0 |
| Oil | 32.5 | 32.5 | 32.5 |
| Product of Example 1 | — | 2.0 | 3.0 |
| TOTAL | 204.5 | 206.5 | 207.5 |
| Second Pass Mix | | | |
| Masterbatch from First Pass (MB-1) | 204.5 | 206.5 | 207.5 |
| Zinc oxide | 2.5 | 2.5 | 2.5 |
| Stearic acid | 1.0 | 1.0 | 1.0 |
| 6-PPD | 2.0 | 2.0 | 2.0 |
| Wax | 1.5 | 1.5 | 1.5 |
| TOTAL | 211.5 | 213.5 | 214.5 |
| Third Pass Mix | | | |
| Masterbatch from Second Pass (MB-2) | 211.5 | 213.5 | 214.5 |
| TBBS | 1.5 | 1.5 | 1.5 |
| Sulfur 21–10 | 2.0 | 2.0 | 2.0 |
| TOTAL | 215.0 | 217.0 | 218.0 |

In the above table, all of the units of the quantities are parts per hundred parts of rubber (phr).

The data in Table 2 below demonstrate the effectiveness of the compounds of this invention. Inclusion of the test material from Example 1 produces a distinct reduction in the tan δ value of the rubber compared to that of rubber without the additive. Although the presence of the test material reduces the cure time needed to attain a full cure, there is not much effect on the scorch safety of the rubber compounds. The stress-strain properties of the specimens containing the test material are hardly affected by the presence of the test materials

TABLE 2

|  | A | B | C |
|---|---|---|---|
| Product of Example 1 | Blank | 2.00 | 3.00 |
| Rheometer - ODR 2000 @ 160° C. | | | |
| $M_L$, Nm | 1.01 | 1.02 | 1.05 |
| $M_H$, Nm | 4.20 | 3.78 | 3.76 |
| ts2, minutes | 5.8 | 5.1 | 4.3 |
| t50, minutes | 8.6 | 6.6 | 5.6 |
| t90, minutes | 11.8 | 8.2 | 7.2 |
| Mooney Viscosity ML 1' + 4' @ 100° C. | | | |
|  | 77 | 78 | 83 |
| Mooney Scorch MS @ 135° C. | | | |
| t3, minutes | 20' | 20' | 16' |
| Stress/Strain | | | |
| Cure times @ 160° C. | 20' | 15' | 15' |
| 100% Modulus Mpa | 2.40 | 2.30 | 2.50 |
| 300% Modulus Mpa | 12.00 | 11.70 | 13.20 |
| Tensile Mpa | 18.30 | 19.10 | 19.50 |
| % Elongation | 430 | 440 | 390 |
| Hardness, Shore A | 63 | 61 | 61 |
| TAN δ | | | |
| RPA 2000 @ 60° C., 10 Hz | | | |
| % Strain | | | |
| 0.7 | 0.140 | 0.119 | 0.112 |
| 1 | 0.168 | 0.144 | 0.143 |
| 2 | 0.223 | 0.197 | 0.181 |
| 5 | 0.260 | 0.227 | 0.208 |
| 7 | 0.259 | 0.226 | 0.216 |
| 14 | 0.245 | 0.217 | 0.212 |
| G'kPa | | | |
| % Strain | | | |
| 0.7 | 5463 | 3925 | 3695 |
| 1 | 5028 | 3563 | 3394 |
| 2 | 3787 | 2836 | 2765 |
| 5 | 2393 | 2052 | 2025 |
| 7 | 2108 | 1808 | 1801 |
| 14 | 1636 | 1469 | 1475 |

EXAMPLE 5

In this example, rubber compositions A, B, and H were mixed up to a temperature of 320° F. (160° C.) and then discharged. Compositions C, D, and F were mixed at 320° F. for 3 minutes and then discharged. Compositions E and G were mixed at 340° F. (about 171° C.) for 3 minutes and discharged. Details of the compositions are shown in Table 3.

TABLE 3

|  | A | B | C | D | E | F | G | H |
|---|---|---|---|---|---|---|---|---|
| First Pass Mix | | | | | | | | |
| SSBR | 75.0 | 75.0 | 75.0 | 75.0 | 75.0 | 75.0 | 75.0 | 75.0 |
| BR | 25.0 | 25.0 | 25.0 | 25.0 | 25.0 | 25.0 | 25.0 | 25.0 |
| N234 Carbon Black | 72.0 | 72.0 | 72.0 | 72.0 | 72.0 | 72.0 | 72.0 | 72.0 |
| Oil | 32.5 | 32.5 | 32.5 | 32.5 | 32.5 | 32.5 | 32.5 | 32.5 |
| Product of Example 1 |  | 3.0 | 3.0 |  |  |  |  |  |
| Product of Example 2 |  |  |  | 3.0 | 3.0 |  |  |  |
| Product of Example 3 |  |  |  |  |  | 3.0 | 3.0 |  |
| 4-Nitroso-diphenylamine |  |  |  |  |  |  |  | 3.0 |
| TOTAL | 204.5 | 207.5 | 207.5 | 207.5 | 207.5 | 207.5 | 207.5 | 207.5 |
| Second Pass Mix | | | | | | | | |
| MB-1 | 204.5 | 207.5 | 207.5 | 207.5 | 207.5 | 207.5 | 207.5 | 207.5 |
| Zinc oxide | 2.5 | 2.5 | 2.5 | 2.5 | 2.5 | 2.5 | 2.5 | 2.5 |
| Stearic acid | 1.0 | 1.0 | 1.0 | 1.0 | 1.0 | 1.0 | 1.0 | 1.0 |
| 6-PPD | 2.0 | 2.0 | 2.0 | 2.0 | 2.0 | 2.0 | 2.0 | 2.0 |
| Wax | 1.5 | 1.5 | 1.5 | 1.5 | 1.5 | 1.5 | 1.5 | 1.5 |
| TOTAL | 211.5 | 214.5 | 214.5 | 214.5 | 214.5 | 214.5 | 214.5 | 214.5 |
| Third Pass Mix | | | | | | | | |
| MB-2 | 211.5 | 214.5 | 214.5 | 214.5 | 214.5 | 214.5 | 214.5 | 214.5 |
| TBBS | 1.5 | 1.5 | 1.5 | 1.5 | 1.5 | 1.5 | 1.5 | 1.5 |
| Sulfur 21–10 | 2.0 | 2.0 | 2.0 | 2.0 | 2.0 | 2.0 | 2.0 | 2.0 |
| TOTAL | 215.0 | 218.0 | 218.0 | 218.0 | 218.0 | 218.0 | 218.0 | 218.0 |

The units of the quantities in Table 3 are parts per hundred of rubber (phr).

This example demonstrates the advantages of the compounds of this invention. Additionally, it demonstrates the effects of mix time and mixing temperature on the final properties of the rubber compounds that include the test materials. As a comparative example 4-nitrosodiphenylamine is also included, (rubber composition H). The results are shown in Table 4.

In each case, inclusion of the test materials in the first pass mix produced rubber with distinctly lower tan δ compared to the blank, compound A. Generally, the improvement in tan δ is increased by increasing either the mix time or the mix temperature. Scorch time is also shown to be sensitive to the mix time and temperature. It is useful to compare the scorch times of the test materials of this invention to that of 4-nitrosodiphenylamine, a material that has been shown to be effective in promoting interaction between rubber polymers and carbon black. Inclusion of 4-nitrosodiphenylamine produced cured compounds with reduced tan δ, but the scorch time was dramatically affected, to the extent that the resulting uncured rubber compound would be nearly useless. The effect of the test materials on the scorch time was far less than that of the known material, while producing a substantial reduction in hysteresis.

In view of the many changes and modifications that can be made without departing from principles underlying the invention, reference should be made to the appended claims for an understanding of the scope of the protection to be afforded the invention.

What is claimed is:

1. A composition of matter comprising a compound of the formula $A_nR$, wherein:

A is

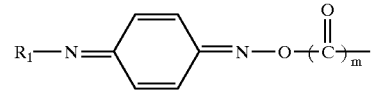

$R_1$ is hydrocarbyl;
m is 0 or 1;
n is 1, 2, or 3;
R is selected from the group consisting of:
mono-, di-, and trivalent aliphatic groups; mono-, di-, and trivalent aromatic groups; five- and six-membered hetero-

TABLE 4

|  | A | B | C | D | E | F | G | H |
|---|---|---|---|---|---|---|---|---|
| Mix Time at Temperature, minutes | 0 | 0 | 3 | 3 | 3 | 3 | 3 | 0 |
| Mix Temperature, ° C. | 160 | 160 | 160 | 160 | 170 | 160 | 170 | 160 |
| Product of Example 1 |  | 3.0 | 3.0 |  |  |  |  |  |
| Product of Example 2 |  |  |  | 3.0 | 3.0 |  |  |  |
| Product of Example 3 |  |  |  |  |  | 3.0 | 3.0 |  |
| 4-Nitrosodiphenylamine |  |  |  |  |  |  |  | 3.0 |
| | | Rheometer - ODR 2000 @ 160° C. | | | | | | |
| $M_L$, Nm | 0.96 | 0.94 | 0.92 | 0.92 | 0.91 | 0.84 | 0.87 | 0.83 |
| $M_H$, Nm | 4.39 | 3.81 | 3.78 | 4.45 | 4.36 | 4.14 | 4.13 | 3.36 |
| ts2, minutes | 5.6 | 4.5 | 4.4 | 4.8 | 4.9 | 4.6 | 4.4 | 1.2 |
| t50, minutes | 8.5 | 5.8 | 5.6 | 6.9 | 6.9 | 6.6 | 6.3 | 2.0 |
| t90, minutes | 11.3 | 7.2 | 7.0 | 9.9 | 10.0 | 9.1 | 8.9 | 3.9 |
| | | Mooney Viscosity ML 1' + 4' @ 100° C. | | | | | | |
| | 78 | 77 | 77 | 77 | 75 | 70 | 71 | 63 |
| | | Mooney Scorch MS @ 135° C. | | | | | | |
| t3, minutes | 21' | 18' | 16' | 15' | 17' | 17' | 15' | 4' |
| | | Stress/Strain | | | | | | |
| Cure Time @ 160° C., minutes | 13' | 13' | 13' | 13' | 13' | 13' | 13' | 7' |
| 100% Modulus, Mpa | 2.3 | 2.3 | 2.3 | 2.9 | 2.8 | 3.1 | 2.9 | 2.5 |
| 300% Modulus, Mpa | 12.0 | 10.4 | 11.0 | 13.5 | 13.2 | 14.2 | 14.4 | 11.5 |
| Tensile Mpa | 20.1 | 17.5 | 17.7 | 18.6 | 17.7 | 18.7 | 18.0 | 17.4 |
| % Elongation | 410 | 440 | 440 | 390 | 370 | 370 | 360 | 410 |
| Hardness, Shore A | 59 | 60 | 59 | 63 | 63 | 62 | 60 | 59 |
| | | TAN δ | | | | | | |
| | | RPA 2000 @ 60° C., 10 Hz | | | | | | |
| % Strain | | | | | | | | |
| 0.7 | 0.106 | 0.089 | 0.092 | 0.089 | 0.092 | 0.084 | 0.088 | 0.108 |
| 1 | 0.138 | 0.118 | 0.113 | 0.114 | 0.113 | 0.114 | 0.111 | 0.129 |
| 2 | 0.200 | 0.171 | 0.173 | 0.171 | 0.169 | 0.162 | 0.155 | 0.168 |
| 5 | 0.272 | 0.235 | 0.221 | 0.242 | 0.234 | 0.234 | 0.222 | 0.216 |
| 7 | 0.270 | 0.236 | 0.225 | 0.243 | 0.232 | 0.240 | 0.231 | 0.218 |
| 14 | 0.260 | 0.236 | 0.228 | 0.240 | 0.229 | 0.231 | 0.221 | 0.222 |
| | | G'kPa | | | | | | |
| % Strain | | | | | | | | |
| 0.7 | 6847 | 5417 | 4973 | 6962 | 6090 | 5906 | 5409 | 3672 |
| 1 | 6049 | 4869 | 4590 | 6263 | 5661 | 5230 | 4984 | 3388 |
| 2 | 4793 | 3926 | 3593 | 4776 | 4344 | 4232 | 3984 | 2844 |
| 5 | 2682 | 2492 | 2387 | 2871 | 2689 | 2627 | 2528 | 2037 |
| 7 | 2304 | 2148 | 2030 | 2441 | 2353 | 2198 | 2027 | 1839 |
| 14 | 1673 | 1555 | 1462 | 1684 | 1660 | 1538 | 1495 | 1431 | cyclic rings comprising n carbon atoms bonded to A, at least one nitrogen atom, and, optionally, at least one sulfur atom; and

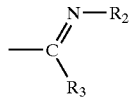

wherein $R_2$ and $R_3$ are independently selected from the group consisting of hydrogen and hydrocarbyl.

2. The composition of claim 1 wherein m is zero and R is selected from the group consisting of five- and six-membered heterocyclic rings comprising n carbon atoms bonded to A, at least one nitrogen atom, and, optionally, at least one sulfur atom; and

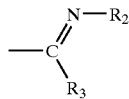

wherein $R_2$ and $R_3$ are independently selected from the group consisting of hydrogen and hydrocarbyl.

3. The composition of claim 2 wherein $R_1$ is selected from the group consisting of phenyl, alkyl-substituted phenyl, alkoxy substituted phenyl, alkyl amino-substituted phenyl, aryl amino-substituted phenyl, naphthyl, alkyl-substituted naphthyl, alkyl, and cyclic alkyl.

4. The composition of claim 3 wherein $R_1$ is phenyl.

5. The composition of claim 2 wherein R is selected from the group consisting of 1,3,5-triazinyl, 2-imidazolyl, 2-pyridinyl, 2-pyrimidinyl, 2-pyrazinyl, 3-pyridazinyl, 2-thiazolyl, 2-quinolyl, 2-quinoxalinyl, 2-quinazolinyl, 2-benzimidazolyl, and 2-benzothiazolyl.

6. The composition of claim 5 wherein R is 1,3,5-triazinyl, n is 1 or 2, and the triazine is substituted with hydroxy, alkoxy, halo, alkylamino, or phenylamino.

7. The composition of claim 3 wherein R is selected from the group consisting of 1,3,5-triazinyl, 2-imidazolyl, 2-pyridinyl, 2-pyrimidinyl, 2-pyrazinyl, 3-pyridazinyl, 2-thiazolyl, 2-quinolyl, 2-quinoxalinyl, 2-quinazolinyl, 2-benzimidazolyl, and 2-benzothiazolyl.

8. The composition of claim 7 wherein R is 1,3,5-triazinyl, n is 1 or 2, and the triazine is substituted with hydroxy, alkoxy, halo, alkylamino, or phenylamino.

9. The composition of claim 4 wherein R is selected from the group consisting of 1,3,5-triazinyl, 2-imidazolyl, 2-pyridinyl, 2-pyrimidinyl, 2-pyrazinyl, 3-pyridazinyl, 2-thiazolyl, 2-quinolyl, 2-quinoxalinyl, 2-quinazolinyl, 2-benzimidazolyl, and 2-benzothiazolyl.

10. The composition of claim 9 wherein R is 1,3,5-triazinyl, n is 1 or 2, and the triazine is substituted with hydroxy, alkoxy, halo, alkylamino, or phenylamino.

11. The composition of claim 2 wherein the compound is 2,4,6-tris(N-phenyl-p-benzoquinonediiminoxy)-1,3,5-triazine.

12. The composition of claim 1 wherein m is 1 and R is selected from the group consisting of mono-, di-, and trivalent aliphatic groups and mono-, di-, and trivalent aromatic groups.

13. The composition of claim 12 wherein $R_1$ is selected from the group consisting of phenyl, alkyl-substituted phenyl, alkoxy substituted phenyl, alkyl amino-substituted phenyl, aryl amino-substituted phenyl, naphthyl, alkyl-substituted naphthyl, alkyl, and cyclic alkyl.

14. The composition of claim 13 wherein $R_1$ is phenyl.

15. The composition of claim 12 wherein R is selected from the group consisting of alkyl, substituted alkyl, alkenyl, alkylidene, alkylene, phenyl, and substituted phenyl.

16. The composition of claim 13 wherein R is selected from the group consisting of alkyl, substituted alkyl, alkenyl, alkylidene, alkylene, phenyl, and substituted phenyl.

17. The composition of claim 14 wherein R is selected from the group consisting of alkyl, substituted alkyl, alkenyl, alkylidene, alkylene, phenyl, and substituted phenyl.

18. The composition of claim 12 wherein the compound is N-{4[(benzoyloxy)imino]-2,5-cyclohexadien-1-ylidene}aniline.

19. The composition of claim 12 wherein the compound is N-{4[(acetyloxy)imino]-2,5-cyclohexadien-1-ylidene}aniline.

20. A composition of matter comprising an elastomer, a filler, and a compound of the formula $A_nR$, wherein:

A is

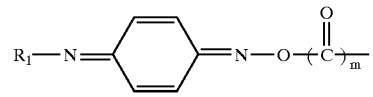

$R_1$ is hydrocarbyl;
m is 0 or 1;
n is 1, 2, or 3;
R is selected from the group consisting of:
mono-, di-, and trivalent aliphatic groups; mono-, di-, and trivalent aromatic groups; five- and six-membered heterocyclic rings comprising n carbon atoms bonded to A, at least one nitrogen atom, and, optionally, at least one sulfur atom; and

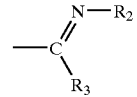

wherein $R_2$ and $R_3$ are independently selected from the group consisting of hydrogen and hydrocarbyl.

21. The composition of claim 20 wherein the filler is carbon black.

22. The composition of claim 21 wherein m is zero and R is selected from the group consisting of five- and six-membered heterocyclic rings comprising n carbon atoms bonded to A, at least one nitrogen atom, and, optionally, at least one sulfur atom; and

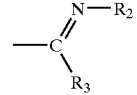

wherein $R_2$ and $R_3$ are independently selected from the group consisting of hydrogen and hydrocarbyl.

23. The composition of claim 22 wherein $R_1$ is selected from the group consisting of phenyl, alkyl-substituted phenyl, alkoxy substituted phenyl, alkyl amino-substituted phenyl, aryl amino-substituted phenyl, naphthyl, alkyl-substituted naphthyl, alkyl, and cyclic alkyl.

24. The composition of claim 23 wherein $R_1$ is phenyl.

25. The composition of claim 22 wherein R is selected from the group consisting of 1,3,5-triazinyl, 2-imidazolyl, 2-pyridinyl, 2-pyrimidinyl, 2-pyrazinyl, 3-pyridazinyl, 2-thiazolyl, 2-quinolyl, 2-quinoxalinyl, 2-quinazolinyl, 2-benzimidazolyl, and 2-benzothiazolyl.

26. The composition of claim 25 wherein R is 1,3,5-triazinyl, n is 1 or 2, and the triazine is substituted with hydroxy, alkoxy, halo, alkylamino, or phenylamino.

27. The composition of claim 23 wherein R is selected from the group consisting of 1,3,5-triazinyl, 2-imidazolyl, 2-pyridinyl, 2-pyrimidinyl, 2-pyrazinyl, 3-pyridazinyl, 2-thiazolyl, 2-quinolyl, 2-quinoxalinyl, 2-quinazolinyl, 2-benzimidazolyl, and 2-benzothiazolyl.

28. The composition of claim 27 wherein R is 1,3,5-triazinyl, n is 1 or 2, and the triazine is substituted with hydroxy, alkoxy, halo, alkylamino, or phenylamino.

29. The composition of claim 24 wherein R is selected from the group consisting of 1,3,5-triazinyl, 2-imidazolyl, 2-pyridinyl, 2-pyrimidinyl, 2-pyrazinyl, 3-pyridazinyl, 2-thiazolyl, 2-quinolyl, 2-quinoxalinyl, 2-quinazolinyl, 2-benzimidazolyl, and 2-benzothiazolyl.

30. The composition of claim 29 wherein R is 1,3,5-triazinyl, n is 1 or 2, and the triazine is substituted with hydroxy, alkoxy, halo, alkylamino, or phenylamino.

31. The composition of claim 22 wherein the compound is 2,4,6-tris(N-phenyl-p-benzoquinonediiminoxy)-1,3,5-triazine.

32. The composition of claim 21 wherein m is 1 and R is selected from the group consisting of mono-, di-, and trivalent aliphatic groups and mono-, di-, and trivalent aromatic groups.

33. The composition of claim 32 wherein $R_1$ is selected from the group consisting of phenyl, alkyl-substituted phenyl, alkoxy substituted phenyl, alkyl amino-substituted phenyl, aryl amino-substituted phenyl, naphthyl, alkyl-substituted naphthyl, alkyl, and cyclic alkyl.

34. The composition of claim 33 wherein $R_1$ is phenyl.

35. The composition of claim 32 wherein R is selected from the group consisting of alkyl, substituted alkyl, alkenyl, alkylidene, alkylene, phenyl, and substituted phenyl.

36. The composition of claim 33 wherein R is selected from the group consisting of alkyl, substituted alkyl, alkenyl, alkylidene, alkylene, phenyl, and substituted phenyl.

37. The composition of claim 34 wherein R is selected from the group consisting of alkyl, substituted alkyl, alkenyl, alkylidene, alkylene, phenyl, and substituted phenyl.

38. The composition of claim 32 wherein the compound is N-{4[(benzoyloxy)imino]-2,5-cyclohexadien-1-ylidene}aniline.

39. The composition of claim 32 wherein the compound is N-{4[(acetyloxy)imino]-2,5-cyclohexadien-1-ylidene}aniline.

40. The composition of claim 19 in which the elastomer is selected from the group consisting of an emulsion polymerized styrene-butadiene rubber, a solution polymerized styrene-butadiene rubber, a polybutadiene, a natural rubber, a polyisobutylene, a polyisoprene, and mixtures of the foregoing.

41. The composition of claim 19 in which the compound is added at a level of 0.1 to 10 parts per hundred of elastomer.

42. An article of manufacture comprising a cured mixture comprising an elastomer, a filler, and a compound of the formula $A_nR$, wherein:

A is $$R_1-N=\underset{}{\underset{}{\bigcirc}}=N-O-(C)_m^{\underset{\|}{O}}$$

$R_1$ is hydrocarbyl;
m is 0 or 1;
n is 1, 2, or 3;
R is selected from the group consisting of:
mono-, di-, and trivalent aliphatic groups; mono-, di-, and trivalent aromatic groups; five- and six-membered heterocyclic rings comprising n carbon atoms bonded to A, at least one nitrogen atom, and, optionally, at least one sulfur atom; and $$-\underset{R_3}{\overset{N-R_2}{\underset{}{C}}}$$

wherein $R_2$ and $R_3$ are independently selected from the group consisting of hydrogen and hydrocarbyl.

43. The article of claim 42 wherein said article is a tire tread.

* * * * *